United States Patent [19]

Eknoian

[11] Patent Number: 6,121,375
[45] Date of Patent: Sep. 19, 2000

[54] GELS FORMED BY THE INTERACTION OF POLY(ALDEHYDE) WITH VARIOUS SUBSTANCES

[75] Inventor: Michael Eknoian, Newark, N.J.

[73] Assignee: Hydromer, Inc., Branchburg, N.J.

[21] Appl. No.: 09/248,591

[22] Filed: Feb. 11, 1999

[51] Int. Cl.[7] .............................. C08L 29/04; C08L 39/04
[52] U.S. Cl. .......................... 525/63; 524/501; 524/503; 524/504; 524/514; 524/538; 524/542; 524/57; 524/58; 524/64; 524/66; 524/69; 524/73; 524/74; 524/154; 524/298
[58] Field of Search ..................................... 524/501, 504, 524/542, 503, 514, 538; 525/63, 64, 66, 69, 73, 154, 298, 74, 57, 58

[56] References Cited

U.S. PATENT DOCUMENTS

| | | | |
|---|---|---|---|
| 4,230,772 | 10/1980 | Swift et al. | 428/442 |
| 4,254,008 | 3/1981 | Krsek | 260/33.4 R |
| 4,673,038 | 6/1987 | Sandiford et al. | 166/270 |
| 5,135,755 | 8/1992 | Czech et al. | 424/445 |
| 5,156,601 | 10/1992 | Lorenz et al. | 604/307 |
| 5,206,322 | 4/1993 | Login et al. | 526/264 |
| 5,336,501 | 8/1994 | Czech et al. | 424/445 |
| 5,420,197 | 5/1995 | Lorenz et al. | 525/54.3 |

*Primary Examiner*—Ana Woodward
*Attorney, Agent, or Firm*—Hoffmann & Baron, LLP

[57] ABSTRACT

The present invention, which addresses the needs of the prior art, provides irreversible, hydrophilic gels which can be incorporated into dressing compositions, dermatologically compatible compositions, wound packings, wound dressings, burn dressings, drug delivery dressings, dry films, cosmetic masks and cosmetic wrap dressings. The gels of the invention include a blend of a hydrophilic poly(aldehyde) and a polymer selected from the group consisting of a poly(amide), a poly(amine) and a poly(alcohol).

10 Claims, No Drawings

GELS FORMED BY THE INTERACTION OF POLY(ALDEHYDE) WITH VARIOUS SUBSTANCES

BACKGROUND OF THE INVENTION

1. Field of Invention

The present invention relates to the field of stable, irreversible, hydrophilic gels and more particularly to blends of poly(amide, amine or alcohol) and hydrophilic poly (aldehyde) which can be used in dressings for a variety of applications including cosmetic applications.

2. Description of the Prior Art

It has been known that polyvinyl-pyrrolidone (PVP) complexes with polyurethanes to yield hydrophilic blends which can be used as wound dressings or in cosmetic preparations. For example, U.S. Pat. No. 5,156,601 discloses a dressing which includes a tacky gel of polyurethane and a poly(N-vinyl lactam) such as PVP with a degree of ring opened pyrrolidone groups. U.S. Pat. No. 5,420,197 describes hydrophilic gels formed by poly(N-vinyl lactams) such as PVP with a degree of ring-opened pyrrolidone groups, and chitosans. Other references of general background interest include U.S. Pat. Nos. 5,135,755 and 5,206,322.

Although some of the hydrophilic gels described in the art can be used for wound dressings and other dermatologically compatible applications, many hydrophilic gels known in the art are reversible and have a tendency to cold flow. Accordingly, there is still a need in the art of dressings, implants and dermatological compositions for gels which are irreversible and do not exhibit cold flow.

It is therefore an object of the invention to provide dressing compositions and dermatologically-compatible compositions which include gels having hydrophilic and absorbent properties and which do not exhibit cold flow.

It is a further object to produce gels without a need for expensive equipment and/or processing.

It is another object to provide gels of poly(aldehyde) and poly(alcohol, amine, amide) which can be used in a variety of products such as cavity dressings, drug delivery patches, face masks, implants and wound dressings.

SUMMARY OF THE INVENTION

The present invention, which addresses the needs of the prior art, provides irreversible, hydrophilic gels which can be incorporated into dressing compositions, dermatologically compatible compositions, wound packings, wound dressings, burn dressings, drug delivery dressings, dry films, cosmetic masks and cosmetic wrap dressings. The gels of the invention include a blend of a hydrophilic poly (aldehyde) and a polymer selected from the group consisting of a poly(amide), a poly(amine) and a poly(alcohol).

The hydrophilic poly(aldehydes) useful in preparing the gels of the invention include, but not limited to, a homopolymer, a copolymer or a terpolymer of acrolien, vinyl formal, glutaric dialdehyde and mixtures thereof. Poly(amides) useful in forming the gels of the invention include, but not limited to, a homopolymer, copolymer or terpolymer derived from acrylamide, N-vinyl lactams, N-vinyl formal and mixtures thereof. Poly(amines) useful in preparing the gels of the present invention include, but not limited to, a homopolymer, copolymer or terpolymer derived from ethylene diamine, allylamine, vinyl pyridine, N-vinyl formal, chistosan, vinyl amine and mixtures thereof. Poly(alcohols) useful in the present invention include a homopolymer, copolymer or terpolymer derived from hydrolyzed poly(vinyl acetate), allyl alcohol, cellulose, ethylene glycol, ethylene oxide and mixtures thereof.

The gel preferably includes at least one additional ingredient which may be releasable from the gel. Preferably, the releasable ingredient is a fragrance or a bioeffecting or body-treating material.

The dressing compositions of the present invention have the advantage of self-adhesion to the skin but with facile peelability. As a result of the present invention, gels are provided which are stable even in hot water, are capable of absorbing many times their weight in water, and are capable or delivering medicaments externally to the body exactly where desired. Most importantly, the products based on the gels of the present invention have the unexpected property of resisting cold flow.

Other improvements which the present invention provides over the prior art will be identified as a result of the following description which sets forth the preferred embodiments of the present invention. The description is not in any way intended to limit the scope of the present invention, but rather only to provide a working example of the present preferred embodiments. The scope of the present invention will be pointed out in the appended claims.

DETAILED DESCRIPTION

The present invention is an irreversible, hydrophilic gel used in dressing compositions, wound packings, wound dressings, burn dressing, drug delivery dressings, dry films, cosmetic mask dressings and cosmetic wrap dressings. The stable, irreversible, hydrophilic gel of the invention includes a two component blend. One component is a hydrophilic poly(aldehyde) and the other is a poly(amide), poly(amine) or poly(alcohol).

The hydrophilic poly(aldehyde) is obtained by grafting aldehyde monomers onto poly(N-vinyl lactams). Aldehyde monomers include without limitations acrolien, vinyl formal and glutaric aldehyde. These compounds are readily commercially available from Aldrich Chemical Co. as an example.

In its monomeric form, acrolein is very reactive and rather toxic. When grafted onto a long chain biocompatible polymer such as, for example, polyvinyl pyrrolidone (PVP) or polyethylene glycol (PEG), a hydrophilic, highly reactive, nontoxic, large poly(aldehyde) is obtained.

In addition to PVP, other suitable homopolymers, copolymers and terpolymers of N-vinyl lactams can be used in the preparation of the hydrophilic poly(aldehyde) of the present invention.

The term poly(N-vinyl lactam) as used herein shall be understood to include, but not limited to, homopolymers, copolymers and terpolymers of N-vinyl lactams such as N-vinylpyrrolidone, N-vinylbutyrolactam, N-vinylcaprolactam, and the like, as well as the foregoing prepared with minor amounts, for example, up to about 20 weight percent, of one or mixture of other vinyl monomers copolymerizable with the N-vinyl lactams. Copolymers or terpolymers of poly(N-vinyl-lactam) may comprise N-vinyllactam monomers such as vinylpyrrolidone copolymerized with monomers containing a vinyl functional group such as acrylates, hydroxyalkylacrylates, methacrylates, acrylic acid or methacrylic acid, and acryl-amides. Of the poly(N-vinyl lactam) homopolymers, the polyvinylpyrrolidone (PVP) homopolymers are preferred. Of the poly(N-vinyl lactam) copolymers, vinyl pyrrolidone, acrylamide copolymers are preferred. Suitable poly(N-vinyl lactam) terpolymers, but not limited to, is vinylpyrrolidone, vinylcaprolactam, and dimethylaminoethyl methacrylate. A variety of polyvinylpyrrolidones are commercially available.

A lactam may be considered to be a cyclic amide produced from an amino acid through the elimination of a molecule of water from the —COOH and —$NH_2$ groups. A lactam, therefore, contains a —NH—CO— group in a ring. An N-vinyl lactam has a vinyl group at the ring nitrogen and the monomer can be polymerized through the vinyl group.

It has been unexpectedly found that when the large, reactive hydrophilic poly(aldehyde) obtained by grafting monomeric aldehydes onto poly(N-vinyl lactams) is mixed with polymers bearing alcohol, amide or amine functionalities, a hydrophilic, irreversible gel, with no leachable aldehydes is formed. As used herein, "hydrophilic" means having a strong tendency to bind or absorb water which results in swelling and formation of gels. Further, as used herein "irreversible gel" means a material which does not loose its structural integrity upon heating, irradiation, or mild chemical additions such as, for example, agar, and poly(acrylamide) gels.

It has also been surprisingly found that the hydrophilic, irreversible gels of the present invention have the very valuable property of being able to resist cold flow.

"Cold flow" refers to creep at room temperature. Due to its viscoelastic nature, plastic materials subjected to a load for a period of time tend to deform more than they would from the same load released immediately after application. The degree of this deformation increases with the duration of the load and with rising temperature. Creep is the permanent deformation resulting from prolonged application of a stress below the elastic limit. This deformation, after any time under stress, is partly recoverable (primary creep) upon the release of the load and partly unrecoverable (secondary creep). As used herein "cold flow" refers to the property of the irreversible gels of the present invention to loose its structure over time due to the applied force of gravity.

Polymers bearing alcohol, amide or amine functionalities refer to, but not limited to, poly(alcohols), poly(amides) and poly(amines) also including natural poly(alcohols), poly (amides) and poly(amines). Poly(alcohols) useful in reacting with poly(aldehydes) to form the hydrophilic irreversible gels of the present invention include, but are not limited to, commercially available hydrolyzed poly(vinyl acetate), allyl alcohol, cellulose, ethylene glycol, ethylene oxide and mixtures thereof.

Useful poly(amides) include, but are not limited, to commercially available acrylamide, N-vinyl lactams, N-vinyl formal and mixtures thereof.

Poly(amines) useful in the formation of the gels of the present invention include, but are not limited to, commercially available ethylene diamine, allyl amine, vinyl pyridine and chitosan.

To form the gel, an aqueous solution of poly(N-vinyl lactam) is mixed with a polymerizable aldehyde to form an aqueous solution of a hydrophilic poly(aldehyde). The aqueous solution of poly(N-vinyl lactam) contains from about 5% to about 50% poly(N-vinyl lactam). The resulting aqueous solution of hydrophilic poly(aldehyde) contains from about 5% by weight to about 50% by weight poly(aldehyde). The resulting poly(aldehyde) is then mixed with an aqueous solution of poly(amine), poly(alcohol) or poly(amide) in a ratio from about 12:1 by weight to about 1:1 by weight to produce a blend having a total polymer content from about 1 weight percent to about 50 weight percent, and preferably from 5% weight to 15 weight %, of poly(aldehyde), poly (amine), poly(amide) and poly(alcohol).

The aqueous solution of poly(amine) contains from about 5% by weight to about 50% by weight poly(amine). The aqueous solution of poly(amide) contains from about 5% by weight to about 50% by weight of poly(amide). The aqueous solution of poly(alcohol) contains from about 5% by weight to about 50% by weight poly(alcohol).

The resulting blend is allowed to cure for a time from about 10 seconds to about 2 hours until a hydrophilic, irreversible gel is formed. The time and temperature for curing are not critical. For purposes of convenience, ambient temperature may be used but the time can be shortened at elevated temperatures. The term gel is intended to mean viscous or semi-solid and jelly-like. The gels of the present invention are stable and therefore irreversible and water insoluble, even in boiling water or alcohol. The gels are hydrophilic and capable of absorbing many times their weight in water or at least 100% their weight in water. Herein the term "tacky" is intended to mean having the property of being sticky to the touch or adhesive to a degree that the gel is capable of sticking to the skin while being easily removable when removal is desired.

While the exact nature of the mechanism by which the gel forms is not known, and while it is not intended to be bound by theory, it is believed that the addition of poly(aldehyde) to a polymer compound bearing amine, amide or alcohol functionalities gives rise to covalent cross-linking dispersed through an interconnecting network of ionic bonds present in the poly(amide), poly(amine) or poly(alcohol).

Many different types of additional materials may be incorporated into the gels of the present invention including organic salts, inorganic salts at low concentrations, alcohols, amines, polymer lattices, fillers, surfactants, pigments, dyes, fragrances and so forth as long as they do not interfere with gel formation. Many of these materials can be released directly from the gel.

The gels of this invention are especially useful as carriers for a wide variety of releasable biologically-active substances having curative or therapeutic value for human or non-human animals. Included among the biologically-active materials which are suitable for incorporation into the gels of the invention are hormones, hypnotics, sedatives, tranquilizers, anti-convulsants, muscle relaxants, analgesics, antipyretic agents, anti-inflammatory agents, local anesthetics, antispasmodics, antiulcer agents, antivirals, antibacterials, antifungals, sympathomimetic agents, cardiovascular agents, antitumor agents, and so forth. A biologically-active substance is added in pharmaceutically-active amounts.

Particularly preferred as biologically-active additives are nitroglycerine, scopolamine, pilocarpine, ergotamine tartrate, phenylpropanolamine, and theophylline; also antimicrobials such as tetracycline, neomycin, oxytetracycline, triclosan, sodium cefazolin, silver sulfadiazine, and also salicylates such as methylsalicylate and salicyclic acid, nicotinates such as methyl nicotinate; capsaicin, benzocaine, α-hydroxy acids, vitamins and biostats.

When the gel is to be used for cosmetic treatment, hydrating agents such as sodium pyrrolidine carboxylic acid, polyols, and polymers may be added. For a hydrating purpose, however, the large amount of water alone which can be absorbed by the hydrophilic gel serves a hydrating function to the skin.

Water-soluble and water-insoluble additives such as those described above may be initially mixed with the aqueous solvent before the gel preparation is begun, may be mixed with the aqueous solution of poly(N-vinyl lactam) or mixed with the aqueous solution of poly(amine), poly(amide) or poly(alcohol) during the gel preparation. Water-soluble ingredients are preferably mixed in with the PVP prior to admixing with the amine, amide or alcohol functionality bearing polymer. One can also emulsify water insolubles by adding surfactants to either the poly(N-vinyl lactam) or poly(amine), poly(amide) or poly(alcohol). Alternatively, additives may be similarly mixed into the gel preparation after the poly(N-vinyl lactam) is blended with the poly (amine), poly(amide), poly(alcohol). Additives may also be applied to the surface of a gel dressing, for example, by spraying, dipping, brushing or rolling.

The gel may be used to make adsorbent wound packing agents or dressings, skin masks or wraps, drug delivery patches, implants and dry film products.

When the gel is used as a wound packing or cavity-filling wound dressing, it advantageously provides the desired properties of such dressings, such as (1) biocompatability; (2) ability to conform to a wound cavity; (3) non-adherence to the wound; (4) ability to absorb exudate; (5) ability to remove in one piece from the wound; (6) ability to hold its physical integrity when swollen with exudate; (7) ease of handling because it is not too sticky.

When used as a skin-hydrating mask, the gel has excellent hydrating capacity, advantageously contains no alcohol, and is easily and cleanly removed.

When used as an implant, the gel has excellent ability to maintain its physical integrity under different conditions, such as heat and aqueous. The gel is also biocompatible which makes it an excellent candidate as an implant.

When made into a dry film and used as a skin mask, it provides a flexible, clear, hydrophilic film which adheres to the skin when wetted with water. The film can retain active moisturizers and other ingredients close to the skin, helping in their delivery. The film can also be easily peeled off after a period of time without leaving residues.

To obtain the products of the invention, the gel may be packaged by itself in a mold, in a dry film form, or as a two-part system which requires mixing prior to use; or may be provided on a substrate and covered with a release liner to prevent the gel from sticking to itself. The release line is removed prior to application to skin.

The substrate may fulfill one or several functions including providing reinforcement, providing a gas and liquid barrier, providing a support with air permeability, providing protection for the gel and the area of treatment, and the like. Substrate selection to provide the desired properties is known to those skilled in the art. Useful substrates include but are not limited to a polymer film, a collagen film, or woven fabric, a non-woven fabric and mixtures thereof. Preferred substrates include a polyurethane or a polyester film, a stretchable material, a release liner and mixtures thereof.

The gel may be coated or spread onto a backing or substrate by any means known in the art. The gel can be combined with or adhered to a virtually unlimited variety of substrates or backings including resins, metal foils, woven and non-woven webs of natural and synthetic fibers, etc. A backing which provides gas and liquid barrier properties may be a polymer film such as polyurethane. Desirable composites with the gel may also be made using films of polyester, polyvinyl alcohol, or polyvinylidene chloride. When the gel has a barrier substrate, the resulting structure has particular utility as a wound and burn dressing. Moisture is kept in and excess exudate is absorbed to promote healing but bacteria are prevented from entering the wound or burn area, and microbial stasis may be maintained through the incorporation of an anti-microbial agent into the gel to prevent infection. For ease of use, the tacky gel on a backing is covered with a release liner which may be a silicone-coated film or polyethylene.

The gel may be coated onto the backing so that the gel occupies all or part of the backing surface. If the gel occupies part of the backing surface, non-gel coated areas of the backing may be provided with an additional adhesive. The gel can also contain tackifiers such as polyacids, polyols, and polyamines which can boost tack. A dressing of this type is positioned on the skin so that the additional skin adhesive comes into contact with intact skin while the absorbent gel contacts a wound. The additional adhesive provides a dressing with staying power when the absorbent gel has become substantially saturated with wound exudate thus losing some of its adhesiveness through a dilution effect. In a preferred embodiment the dressing is formed by casting two separate slabs of gel onto two separate substrates, applying a solution of a biologically-active material to a surface of one of the slabs and compressing the slabs together so that the biologically-active material is sandwiched between the two slabs.

In still another embodiment, the gel may be used in a dermatologically-compatible composition for cosmetic preparations and cosmetic wrap dressings. In yet another embodiment, the gel may be used in cosmetic preparations such as face masks and nail wraps. The gel serves a hydrating function with or without a backing and a cosmetic effect may be enhanced with the incorporation of other ingredients. A kit for a cosmetic gel may comprise a ready-made gel or two components: a poly(N-vinyl lactam) component and alcohol, amine or amide functionality bearing polymer component. Other cosmetic agents such as hydrating agents, fragrances, and the like can also be supplied to the ready-made gel or to either component. For use, the components may be mixed and applied. The gel advantageously can be easily peeled off after use. It shall be understood that the term cosmetic means a preparation intended to enhance or improve physical appearance.

In a further embodiment, fragrances may be incorporated into the gel. When the gel is kept moist in a suitable vented container, the fragrance is slowly released as an air freshener.

The following examples are intended to illustrate but not limit the invention. In the following examples irreversible, hydrophilic gels are formed which do not leech aldehydes and can be used as a wound, burn dressing, implants or for cosmetic applications.

EXAMPLE 1

To three separate 250 milliliter round-bottom flasks equipped with a stirrer, reflux condenser and thermometer 99.0 grams of a 10% solution of PVP (Kollidon 90F, BASF) was added to the first flask; (2) 99.0 grams of a 10% solution of poly(ethylene glycol) was added to the second flask; and 99.0 grams of a 10% solution of poly(ethylene diamine) was added to the third flask. The solution was heated to 60° C. with stirring, then 0.5 grams of a water soluble initiator (Wako V-50, Dock Resins Co.) was added to each flask and the solution of each flask was stirred for thirty minutes. 0.5 grams of acrolien, a polymerizable aldehyde manufactured by Aldrich Chemical Co., was then added to each flask and the resulting solution was heated to 75° C. for six hours with stirring. When mixed with polymers with alcohol, amide or amine functionalities, each of the PVP, poly(ethylene glycol), and poly(ethylene diamine) in each flask forms a hydrophilic, irreversible gel, with no leechable aldehydes detected.

EXAMPLE 2

To a 250 milliliter round-bottom flask equipped with a stirrer, reflux condenser and thermometer 99.0 grams of a 25% solution of PEG (Carbowax, Fischer Co.) was added. The solution was heated to 60° C. with stirring, then 0.5 grams of a water soluble initiator (hydrogen peroxide, Aldrich Chemical Co.) was added, and the solution was stirred for thirty minutes. 0.5 grams of a polymerizable aldehyde (acrolien, Aldrich Chemical Co.) was then added and the solution was heated to 75° C. for six hours with stirring. When mixed with polymers with alcohol, amine, or amide functionalities, PEG forms a hydrophilic, irreversible gel, with no leechable aldehydes detected.

EXAMPLE 3

To a 250 milliliter round-bottom flask equipped with a stirrer, reflux condenser and thermometer, was added 99.4 grams of a 10% solution of PVP (Kollidon 90F, BASF) was added. The solution was heated to 60° C. with stirring, then 0.5 grams of a water soluble initiator (sodium persulfate, Aldrich Chemical Co.) was added, and the solution was stirred for thirty minutes. 0.1 grams of a polymerizable aldehyde (acrolien, Aldrich Chemical Co.) was then added and the solution was heated to 75° C. for six hours with stirring. When mixed with polymers with alcohol, amide, or amine functionalities, PVP forms a hydrophilic, irreversible gel, with no leechable aldehydes detected.

EXAMPLE 4

To a 250 milliliter round-bottom flask equipped with a stirrer, reflux condenser and thermometer, 20 grams vinyl pyrrolidone (Aldrich Chemical Co.) and 79 grams water were added. The solution was heated to 60° C. with stirring, then 0.5 grams of a water soluble initiator (Wako V-50) was added, and the solution was stirred for ten minutes. 0.1 grams of a acrolien, a polymerizable aldehyde manufactured by Aldrich Chemical Co., was then added and the resulting solution was heated to 75° C. for six hours with stirring. When mixed with compounds with alcohol, amide, or amine functionalities, PVP forms a hydrophilic, irreversible gel, with no leechable aldehydes detected.

EXAMPLE 5

To a beaker containing 50 grams of a polymer, described in Example 1, 3 grams of lactic acid were added with stirring. Once thoroughly mixed, 47 grams of a 50% solution of Polymin, a poly(amine) manufactured by BASF was added with stirring. The resulting gel was tacky, pliable, incorporated 1.5% lactic Acid, which can be used for cosmetic applications.

EXAMPLE 6

To a beaker containing 50 grams of PVP described in Example 3, was added 50 grams of a dilute chitosan solution was added with stirring. The resulting gel was irreversible at 130° C. and was pliable and relatively non-adherent to a wound. The gel, when put into excess water or saline solution at room temperature, absorbed water but did not dissolve or disintegrate over a period of several days. It was found that the gel absorbed 1,020% of its weight in water or saline. The gel can be used as a wound or burn dressing because it was tacky, but non-adherent to the wound.

EXAMPLE 7

A portion of the gel formed in Example 5 was dried to form a thin flexible film, which was soaked in water at room temperature. The film absorbed 150% water expanding in the process.

Thus, while there have been described what are presently believed to be the preferred embodiments, those skilled in the art will appreciate that other and further changes and modifications can be made without departing from the true spirit of the invention, and it is intended to include all such changes and modifications within the scope of the claims which are appended hereto.

What is claimed is:

1. A stable, irreversible hydrophilic gel which comprises:
   (a) a blend of a hydrophilic poly(aldehyde), which is obtained by grafting aldehyde monomers onto poly(N-vinyl lactams); and,
   (b) a polymer selected from the group consisting of a poly(amide), a poly(amine), a poly(alcohol) and mixtures thereof.

2. The gel of claim 1 wherein said poly(amide), said poly(amine) and said poly(alcohol) are natural polymers.

3. The gel of claim 1 wherein said hydrophilic aldehyde monomers are selected from the group consisting of acrolien, vinyl, formal glutaric aldehyde and mixtures thereof.

4. The gel of claim 1 wherein said poly(amide) comprises a homoploymer, copolymer, or terpolymer derived from a monomer selected from the group consisting of acrylamide, N-vinyl lactams, N-vinyl formal and mixtures thereof.

5. The gel of claim 1 wherein said poly(amine) comprises a homopolymer, copolymer, or terpolymer selected from the group consisting of ethylene diamine, allylamine, vinyl pryridine chitosan and mixtures thereof.

6. The gel of claim 1 wherein said poly(alcohol) comprises a homopolymer, copolymer, or terpolymer selected from the group consisting of hydrolyzed poly(vinyl acetate), allyl alcohol, cellulose, ethylene glycol, ethylene oxide and mixtures thereof.

7. The gel of claim 1 wherein said hydrophilic gel comprises a ratio by weight of poly(aldehyde):poly(amine), poly(aldehyde):poly(amide) from about 12:1 to about 1:1.

8. The gel of claim 7 wherein said hydrophilic gel has a total polymer concentration of from about 1 weight percent to about 50 weight percent of poly(aldehyde), poly(amine), poly(amide), and poly(alcohol).

9. A method for preparing an irreversible, mildly tacky, hydrophilic gel which comprises the steps of (i) mixing an aqueous dissolved poly(aldehyde) obtained by grafting aldehyde monomers onto poly(N-vinyl lactams) and an aqueous solution of a poly(amine), poly(alcohol), or poly(amide) with a total polymer content above 5 weight percent to produce a blend; and (ii) allowing said blend in step (i) to cure until said hydrophilic gel is formed.

10. The method of claim 9 wherein said hydrophilic gel comprises a ratio by weight of poly(aldehyde):poly(amine), poly(aldehyde):poly(alcohol) or poly(aldehyde):poly(amide) from about 12:1 to about 1:1.

* * * * *

UNITED STATES PATENT AND TRADEMARK OFFICE
CERTIFICATE OF CORRECTION

PATENT NO. : 6,121,375
DATED : September 19, 2000
INVENTOR(S) : Eknoian, Michael It is certified that error appears in the above-identified patent and that said Letters Patent is hereby corrected as shown below:

In Columns 8, Line 47-48, reads "comprises a ratio by weight of poly(aldehyde):poly(amine), poly(aldehyde):poly(amide) from about 12:1 to about 1:1."

should read --comprises a ratio by weight of poly(aldehyde):poly(amine), poly(aldehyde):poly(alcohol) or poly(aldehyde):poly(amide) from about 12:1 to about 1:1.--

Signed and Sealed this

Twenty-second Day of May, 2001

Attest:

NICHOLAS P. GODICI

Attesting Officer

Acting Director of the United States Patent and Trademark Office